US012797416B2

(12) United States Patent
Jeong et al.

(10) Patent No.: US 12,797,416 B2
(45) Date of Patent: Nov. 17, 2026

(54) SPHEROIDS FOR SUPPRESSING IMMUNE REJECTION AND USES THEREOF

(71) Applicant: RESEARCH COOPERATION FOUNDATION OF YEUNGNAM UNIVERSITY, Gyeongsan-si (KR)

(72) Inventors: Jee-Heon Jeong, Daegu (KR); Tien Tiep Nguyen, Gyeongsan-si (KR)

(73) Assignee: RESEARCH COOPERATION FOUNDATION OF YEUNGNAM UNIVERSITY, Gyeongsan-si (KR)

( * ) Notice: Subject to any disclaimer, the term of this patent is extended or adjusted under 35 U.S.C. 154(b) by 844 days.

(21) Appl. No.: 17/978,236

(22) Filed: Nov. 1, 2022

(65) Prior Publication Data

US 2023/0165903 A1 Jun. 1, 2023

(30) Foreign Application Priority Data

Sep. 1, 2021 (KR) ........................ 10-2021-0116173

(51) Int. Cl.

*A61K 35/28* (2015.01)
*A61K 9/16* (2006.01)
*A61K 31/436* (2006.01)
*A61K 35/39* (2015.01)
*A61P 3/10* (2006.01)
*A61P 37/06* (2006.01)
*C12N 5/0775* (2010.01)

(52) U.S. Cl.

CPC ............ *A61K 35/28* (2013.01); *A61K 9/1647* (2013.01); *A61K 9/1694* (2013.01); *A61K 31/436* (2013.01); *A61K 35/39* (2013.01); *A61P 3/10* (2018.01); *A61P 37/06* (2018.01); *C12N 5/0667* (2013.01)

(58) Field of Classification Search

None

See application file for complete search history.

(56) References Cited

FOREIGN PATENT DOCUMENTS

KR 10-2011-0134625 A 12/2011

OTHER PUBLICATIONS

Kojima et al. (Biomaterials 33 (2012) 4508-4514).*
Jhunjhunwala et al. (J Control Release Feb. 10, 2009; 133(3): 191-197).*
Manju Shrestha, et al., “Immunomodulation effect of mesenchymal stem cells in islet transplantation”, Biomedicine & Pharmacotherapy, 2021, vol. 142, pp. 112042.
Wu Duan, et al., “Mesenchymal stem cells in combination with low-dose rapamycin significantly prolong islet allograft survival through induction of regulatory T cells”, Biochemical and Biophysical Research Communications, vol. 506, Issue 3, Nov. 30, 2018, pp. 619-625.
Chen Wang, et al., “Rapamycin-treated human endothelial cells preferentially activate allogeneic regulatory T cells”, Journal of Clinical Investigation, Apr. 2013, vol. 123, No. 4, pp. 1677-1693.

* cited by examiner

*Primary Examiner* — Anna R Falkowitz
*Assistant Examiner* — Garen Gotfredson
(74) *Attorney, Agent, or Firm* — Revolution IP, PLLC

(57) ABSTRACT

The present disclosure relates to spheroids for suppressing immune rejection including mesenchymal stem cells and rapamycin microparticles, uses thereof, and a preparation method thereof, wherein the spheroids includes the mesenchymal stem cells and rapamycin microparticles have increased PD-L1 expression of mesenchymal stem cells by the rapamycin microparticles such that the spheroids in which PD-L1 expression on the surface is increased suppress T cells and inflammatory responses that induce immune rejection to the pancreatic islet cells transplanted in vivo, thereby exhibiting the effect of maintaining a survival period and insulin secretion functions of transplanted pancreatic islet cells for a long time.

11 Claims, 7 Drawing Sheets

Specification includes a Sequence Listing.

[FIG. 1]
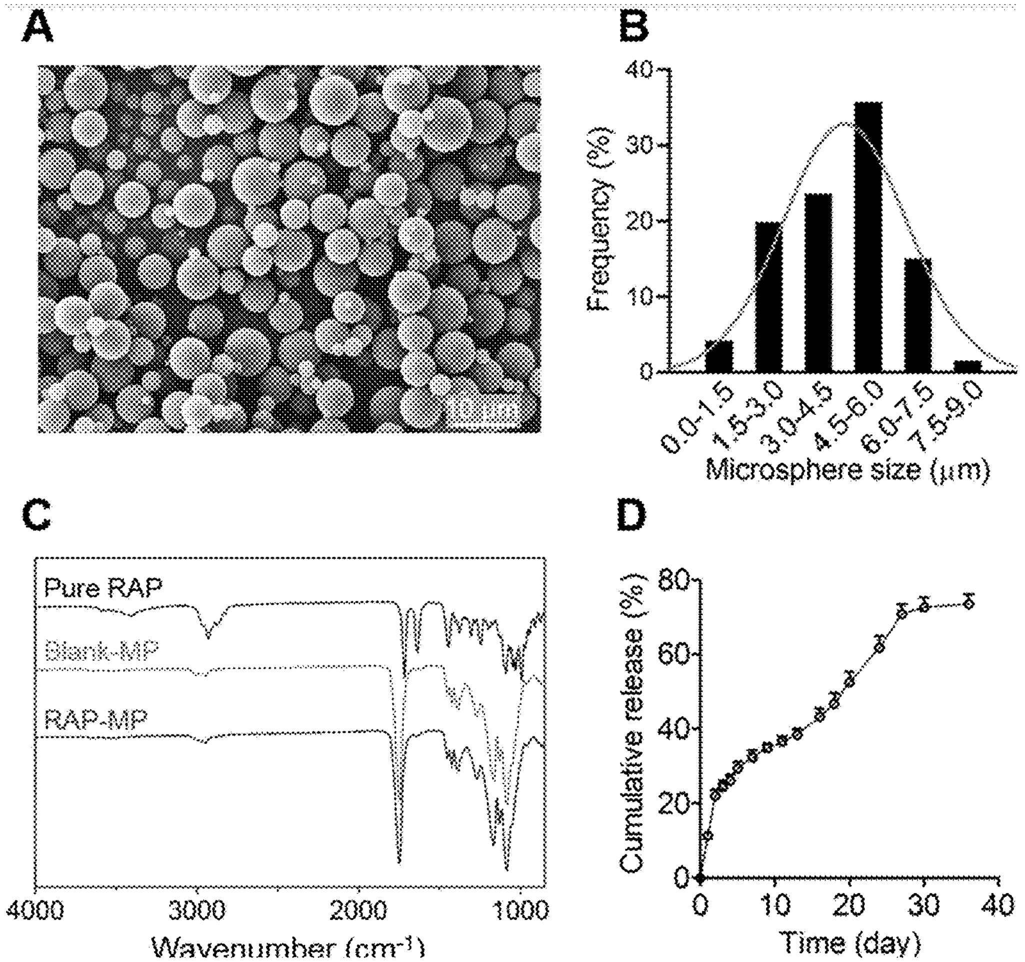

[FIG. 2]
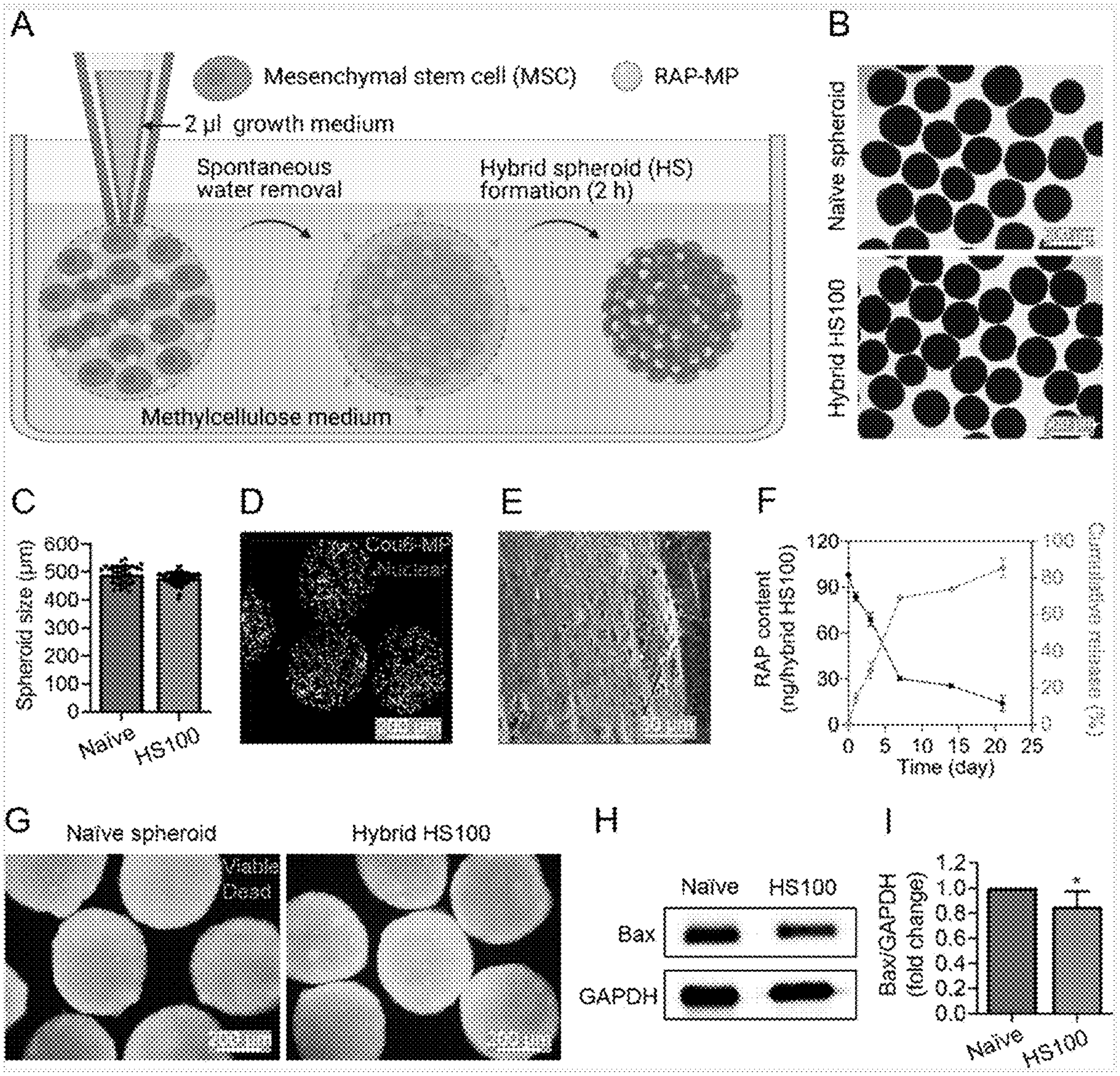

[FIG. 3]
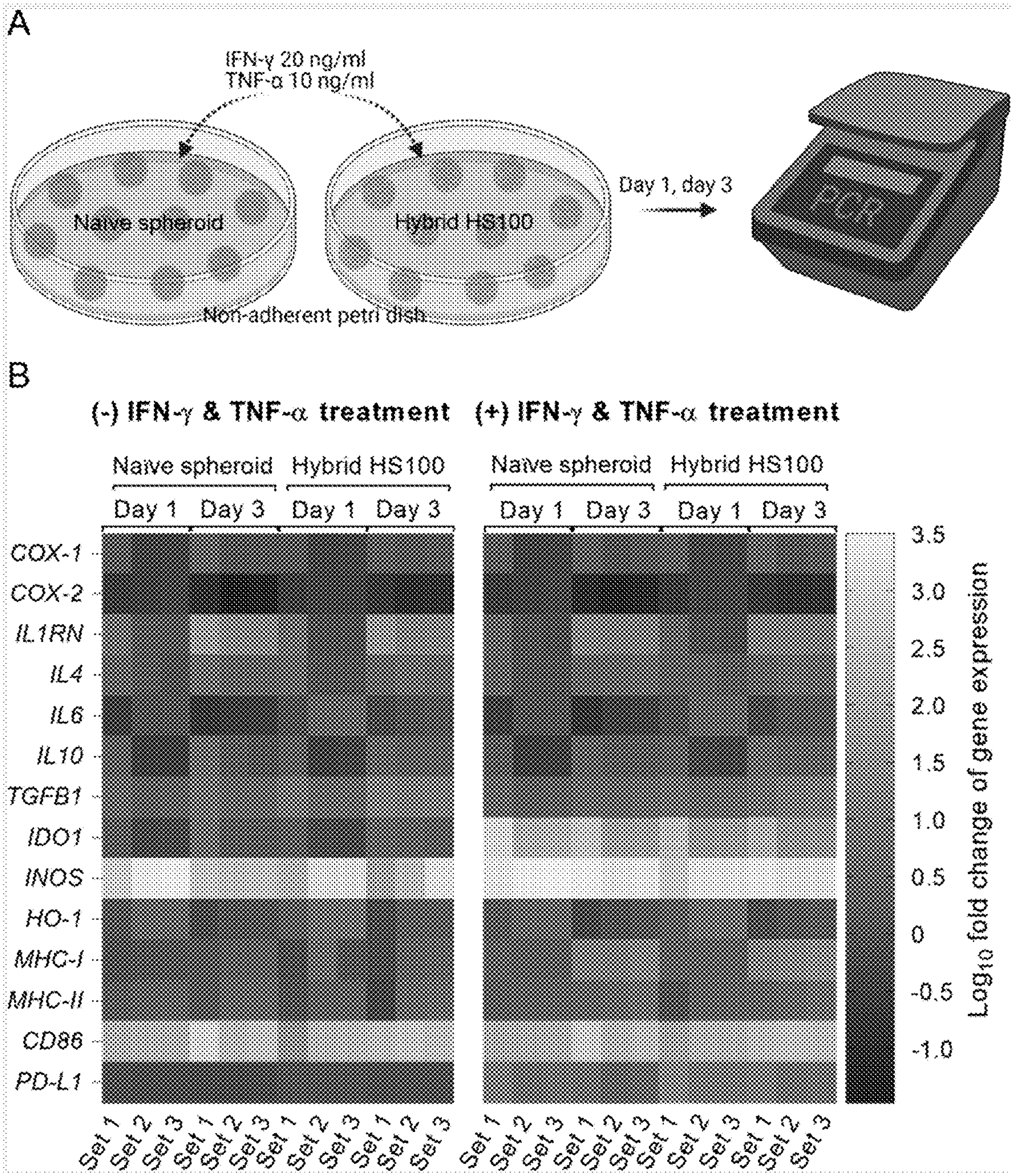

[FIG. 4]
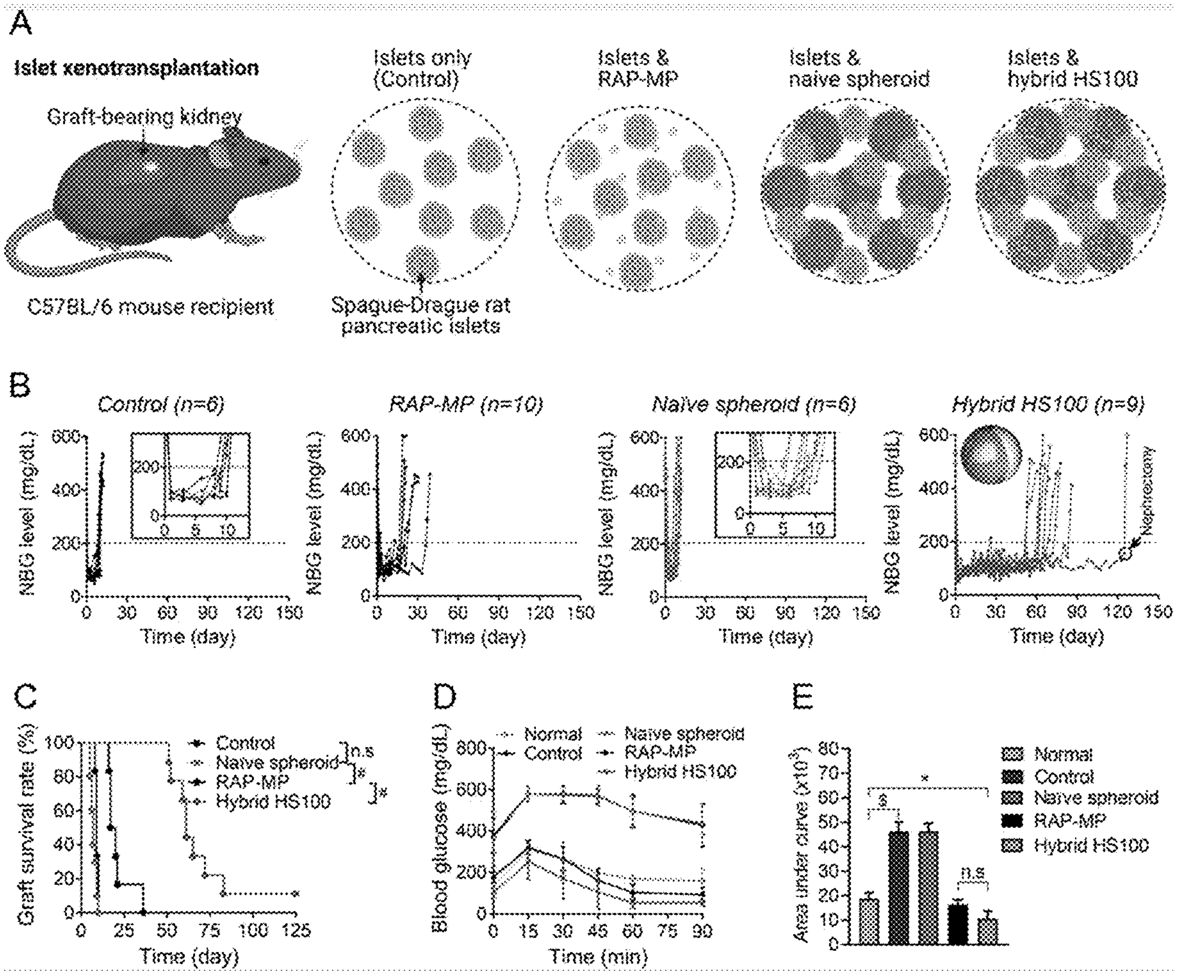

[FIG. 5]
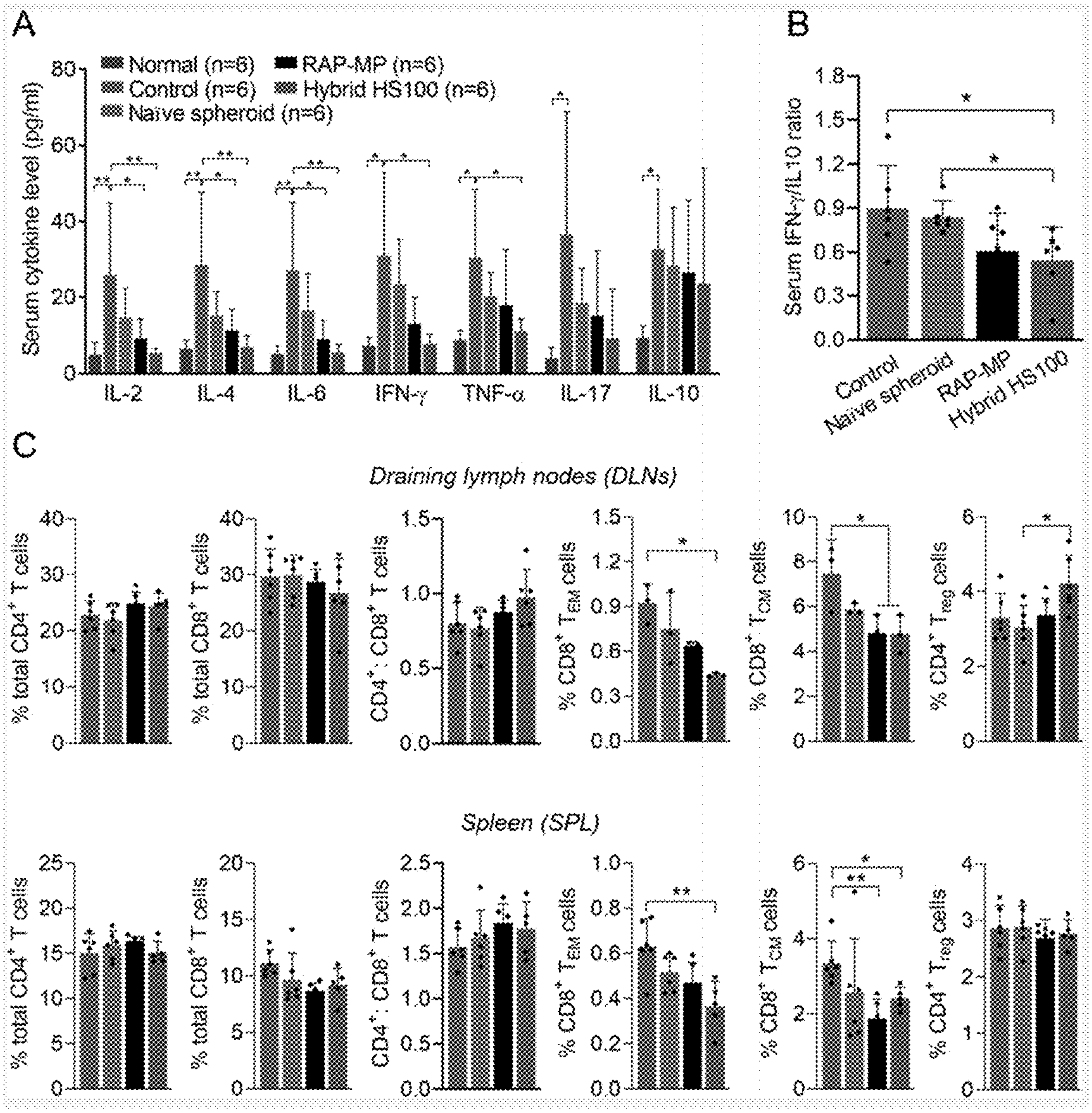

[FIG. 6]
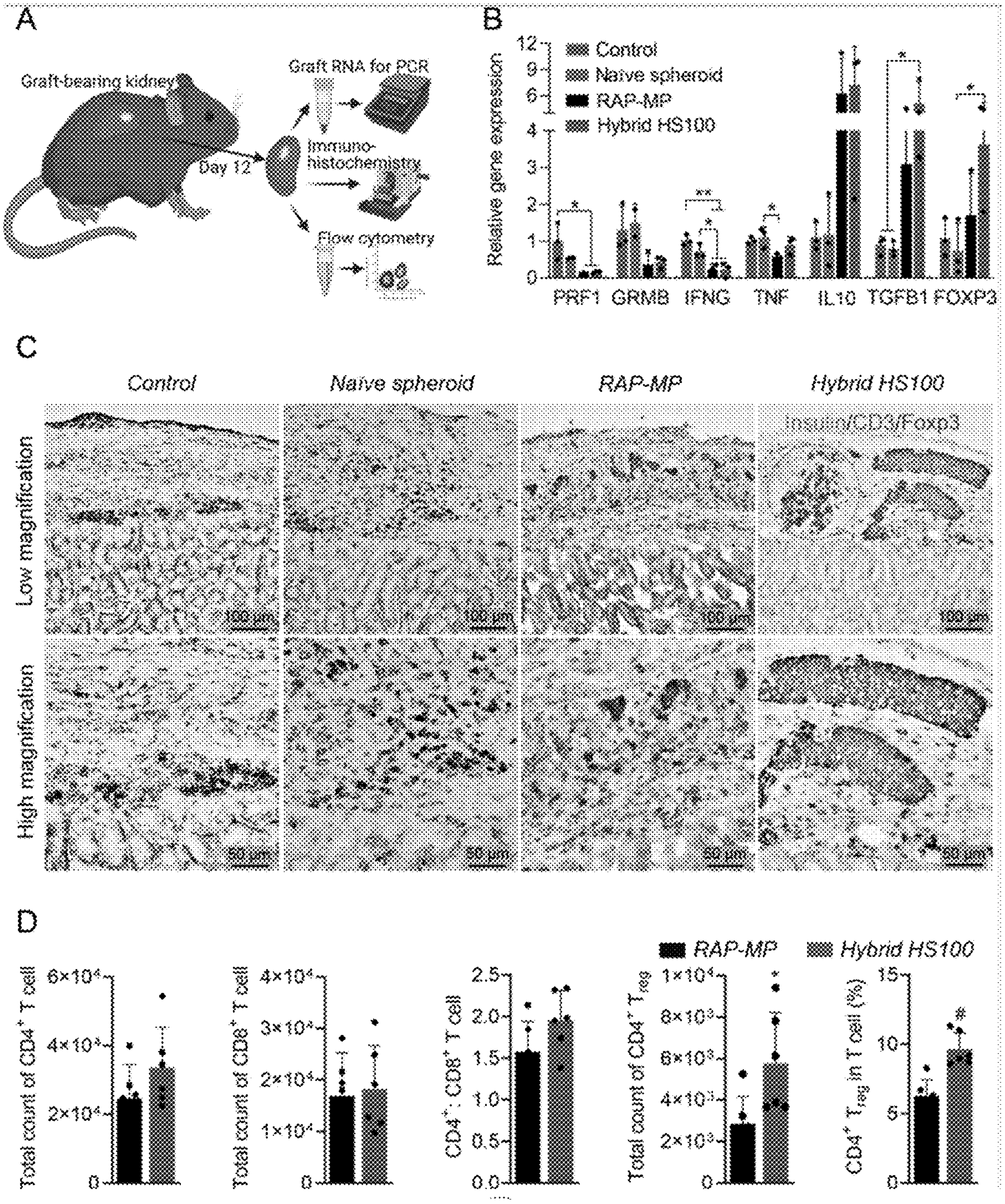

[FIG. 7]
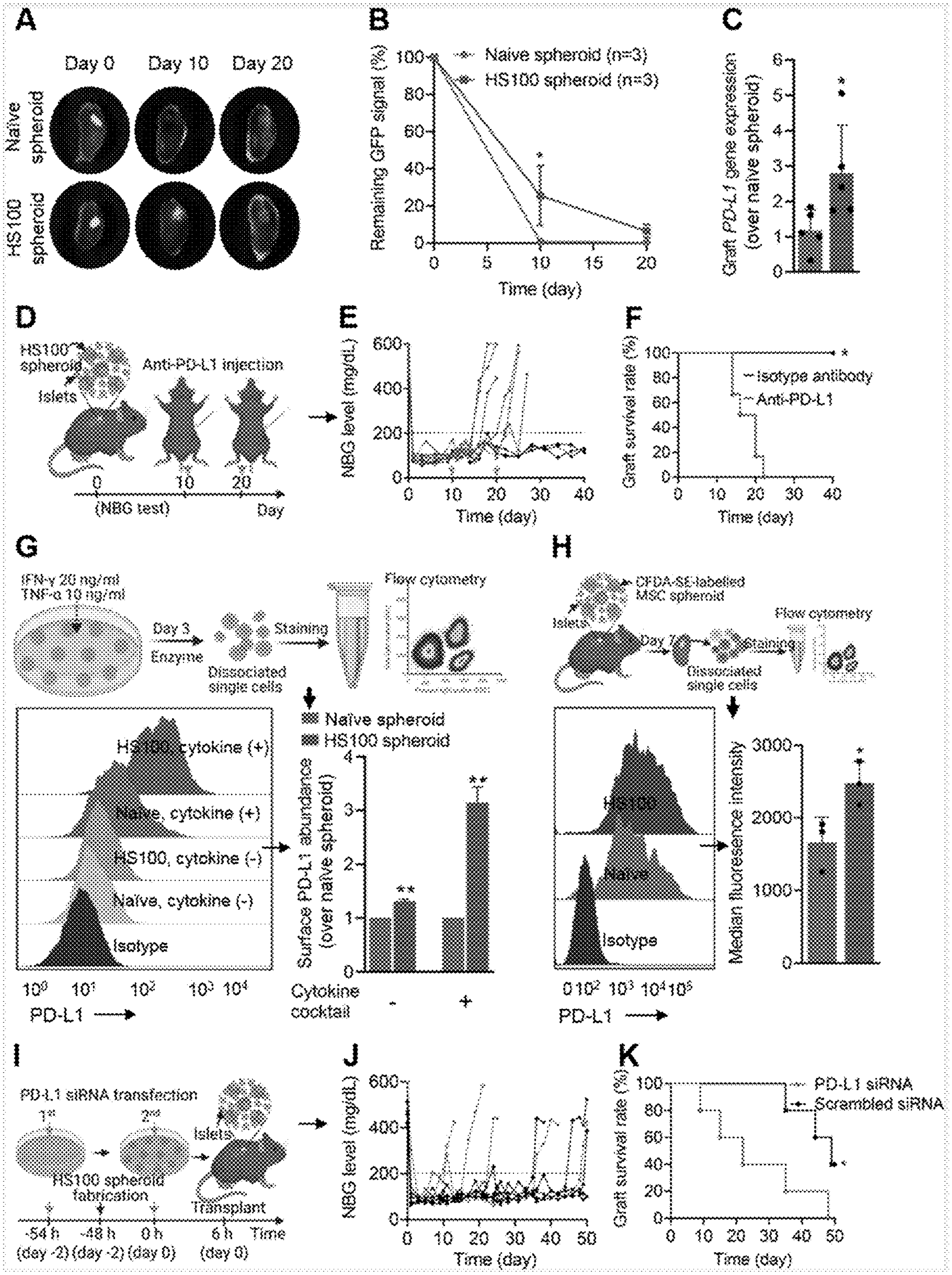

SPHEROIDS FOR SUPPRESSING IMMUNE REJECTION AND USES THEREOF

CROSS-REFERENCE TO RELATED APPLICATION

This application claims the benefit of Korean Patent Application No. 10-2021-0116173 filed on Sep. 1, 2021, in the Korean Intellectual Property Office, the entire disclosure of which is incorporated herein by reference for all purposes.

BACKGROUND

1. Field of the Invention

The present disclosure relates to spheroids for suppressing immune rejection including mesenchymal stem cells and rapamycin microparticles, uses thereof, and a preparation method thereof.

2. Description of the Related Art

Pancreatic islets are a cell mass made up of alpha, beta, and delta cells, which are named as the cells are separated from the pancreas like islands. There among, beta cells are crucial in secreting insulin to regulate blood sugar levels in the blood.

Recently, in order to treat type 1 diabetes, an allogeneic transplantation is being conducted, which is to isolate only insulin-secreting pancreatic islet cells from the pancreas to transplant the same to diabetic patients. Since the Edmonton protocol was developed in 1999, the number of cases of diabetes treatment by allogeneic pancreatic islet transplantation in the United States and Europe has reached 900 cases. Recently, pancreatic islet transplantation has become an important alternative for diabetes treatment, securing 50% of 5-year survival rate of transplanted pancreatic islet cells. However, though this is the best alternative for the treatment of type 1 diabetes, the biggest barrier is the lack of pancreas to transplant.

As an alternative thereto, studies are currently undertaken to transplant pancreatic islet cells isolated from pigs into humans. Porcine pancreatic islet cells are physiologically similar to that of humans, may be obtained in large quantities, and are easy to genetically modify. The potential for treating diabetes using porcine pancreatic islet cells has been demonstrated in several studies using rodents and primates. However, in order to treat diabetes by applying porcine pancreatic islet cells to humans, preclinical studies using primates must be preceded. Since 2005, when the Emory University and the University of Minnesota in the United States transplanted porcine pancreatic islet cells into primates and identified the long-term survival of the transplanted porcine pancreatic islet cells for the first time, 6 groups have reported more than 6 months of survival of transplanted pancreatic islet cells so far. Accordingly, the xenotransplantation community has discovered the clinical applicability of porcine pancreatic islet cell xenotransplantation, and agreed and established international guidelines for clinical application of heterogeneous pancreatic islets through the International Xenotransplantation Association (IXA) in 2009. According to the guidelines, a successful criterion for a preclinical study for clinical application is that normoglycemia or minimal levels of porcine C-peptide should be detected in 5 out of 8 animals for at least 6 months after transplantation of porcine pancreatic islet cell products into diabetic primates. However, there are no research results that satisfy these international guidelines except for immunosuppressive therapy worldwide.

The long-term survival of transplanted pancreatic islet cells in a recipient depends on how effectively they suppress various immune responses that take place against the transplanted pancreatic islet cells. Such the immune response may be divided into an instant blood mediated inflammatory reaction (IBMIR), which mainly occurs within the first few minutes upon transplantation and an immune response by T cells and B cells involved in acute and chronic rejection. Long-term survival of xenotransplanted pancreatic islets depends on how to effectively regulate T cells. Drugs such as MMF, rapamycin, cyclosporine, tacrolimus, leflunomide, Alemtuzumab, CTLA4-Ig, LFA-3-Ig, FTY720, Bortezomib, and CD40-CD40L blockade have been studied to suppress the immune response by T cells. Favorable results have been reported, which may bring hope for the treatment of diabetes by transplanted pancreatic islet cells from rodents and primates using the drugs and combinations thereof. However, in studies targeting primates, which are essential for clinical application, research results with high efficacy that satisfies the IXA guidelines for clinical application have not yet been published. This means that application of theses immunosuppressive therapies to higher animals and humans beyond primates may come out with selective research results rather than with effective and sustainable outcome. In addition, although short-term survival of pancreatic islet cells by T-cell suppression is possible with the combination of conventional immunosuppressive agents, there is a limit in deriving the long-term survival in vivo.

PRIOR ART DOCUMENT

Patent Document

Korean Patent Application Publication No. 10-2011-0134625 (Published on Dec. 15, 2011)

SUMMARY

Problem to be Solved by the Invention

An object of the present disclosure is to provide spheroids for suppressing immune rejection to protect a cell transplant in vivo from immune rejection so as to improve the survival period of the transplant and cellular functionality, and a composition including the spheroids and cells as a cell therapeutic agent.

Means for Solving the Problem

The present disclosure provides spheroids with increased PD-L1 expression, including mesenchymal stem cells and rapamycin microparticles.

The present disclosure provides a composition for suppressing immune rejection including the spheroids as an active ingredient.

The present disclosure provides a method of preparing spheroids for suppressing immune rejection of a transplant, including preparing rapamycin microparticles in which rapamycin is encapsulated with a polymer (first operation); preparing a suspension by mixing the rapamycin microparticles and mesenchymal stem cells in a growth medium (second operation); preparing cell-particle fusion spheroids by injecting the suspension into a polymer solution and then culturing the same (third operation); and collecting the spheroids (fourth operation).

In addition, the present disclosure provides a cell therapy composition for preventing or treating diabetes, including the spheroids and pancreatic islet cells as active ingredients.

Effects of the Invention

It was found that spheroids of the present disclosure including mesenchymal stem cells and rapamycin microparticles have increased PD-L1 expression of the mesenchymal stem cells by rapamycin microparticles such that the spheroids in which PD-L1 expression on the surface is increased suppress T cells and inflammatory responses that induce immune rejection to the pancreatic islet cells transplanted in vivo, thereby exhibiting the effect of maintaining a survival period and insulin secretion functions of transplanted pancreatic islet cells for a long time. Thus, the spheroids including the mesenchymal stem cells and rapamycin microparticles may be provided as a composition for suppressing immune rejection of a cell transplant, and a composition including the spheroids and pancreatic islet cells may be provided as a cell therapeutic agent for treatment of diabetes.

BRIEF DESCRIPTION OF THE DRAWINGS

FIG. 1 shows results of identifying the rapamycin-loaded PLGA microsphere characterization: (A) is the result of a SEM image of RAP-MP; (B) is the result of identifying the size distribution of MP, wherein more than 200 particles were used for size measurement; (C) is the result of the FTIR spectroscopy for pure RAP powder (black line), blank MP (red line), and RAP-MP (blue line); and (D) is the result of in vitro release profile (n=3) of RAP, measured for 35 days from RAP-MP which was cultured in PBS (pH 7.4 and 1% Tween-20) at 37° C. and 100 rpm.

FIG. 2 shows results of identifying preparation and characteristics of hybrid spheroids of mesenchymal stem cells (MSCs) using RAP-MP: (A) is a schematic diagram of a hybrid spheroid methylcellulose-based manufacturing process of mesenchymal stem cells (MSCs) using RAP-MP, wherein spheroids were collected from a methylcellulose solution after 2 hours of culture (day 0) and cultured in the presence of MEM-α medium in non-adherent Petri dishes before evaluation on day 3. A single hybrid spheroid theoretically contains $2.5\times10^4$ MSC and RAP (MP corresponding to 100 ng RAP; i.e., HS100), and RAP-MP-free spheroids were named naïve spheroids; (B) and (C) are the results of measuring images and sizes of naïve spheroids and hybrid HS100 (scale bar: 500 μm); (D) is the result of identifying distribution of the MP labeled with coumarin-6 (Cou6) in hybrid HS100 visualized with a confocal laser scanning microscope (CLSM), wherein cell nuclei were stained with Hoechst 33342 reagent (blue) (scale bar: 200 μm); (E) is an SEM image of the hybrid HS100, wherein the red arrow indicates MP (scale bar: 30 μm); (F) is the result of identifying the actual amount and release ratio (n=3-5) of RAP in the hybrid HS100 in accordance with the culture time; (G) is the result of identifying the cell viability of spheroids using Live/Dead staining analysis (scale bar: 200 μm); and (H) and (I) are the results of evaluating apoptosis in spheroids by measuring the Bax level in Western blot analysis, wherein the Bax level was normalized to each GAPDH level (n=6 independent experiments), and (I) is the result of analyzing the Bax level using an unpaired two-tailed t-test (*p<0.05).

FIG. 3 shows results of identifying the dynamic changes in immune-related gene expression by hybrid spheroids: (A) is a simplified illustration of spheroid culture, treatment and evaluation, wherein naïve spheroids and hybrid HS100 were collected to be subjected to quantitative reverse transcription polymerase chain reaction (qRT-PCR) analysis on days 1-3 of culture after the culture in growth MEM-α medium with or without cytokine cocktails (IFN-γ and TNF-α); and (B) is the result of identifying the gene expression level represented in the type of a heatmap, wherein the data was expressed as a log 10-fold variable for day 0 (n=3 independent sets of experiments).

FIG. 4 shows results of identifying the effect that the local delivery of hybrid spheroids improves the survival of rat-to-mouse pancreatic islet cell xenotransplants: (A) is a graphic illustration of a pancreatic islet cell xenotransplant model, wherein pancreatic islet cells (400 islet equivalents, IEQ) were co-transplanted under the renal capsule of diabetic C57BL/6 mice induced with streptomycin (streptozocin, STZ) with pancreatic islet cells only (control), RAP-MPs, naïve spheroids or hybrid spheroids, wherein 20 spheroids corresponding to $0.5\times10^6$ MSCs were used per transplant, and the RAP dose in the RAP-MP group and the hybrid HS100 group was approximately 1400 ng (~1400 ng) per transplant; (B) is the result of identifying the non-fasting blood glucose (NBG) level of mouse recipients; (C) is the Kaplan-Meier curve for the survival time of pancreatic islet cell xenotransplants; (D) and (E) are intraperitoneal glucose tolerance test (IPGTT) and analysis values of each area under the curve (n=3) at day 12 after transplantation; (C) is the analysis result using the log-rank (Mantel-Cox) test; and (E) is the analysis result using a one-way ANOVA test (*p<0.05, **p<0.01, #p<0.001, $ p<0.0001).

FIG. 5 shows results of identifying the systemic immune response suppression effect of local delivery of hybrid spheroids on pancreatic islet cell transplantation by collecting serum and lymphoid organs on day 12 after transplantation: (A) is the result of identifying the cytokine level in the serum determined by the cytometric bead array (CBA) mouse Th1/Th2/Th17 cytokine kit (n=6); (B) is the result of identifying the serum IFN-α/IL10 ratio; and (C) is the result of identifying the percentage of each T cell population over total cell counts in draining lymph node (DLN) and spleen (SPL) (n=3-6) using flow cytometry, wherein the data in (A) and (C) were analyzed using one-way ANOVA test, and the data in (B) and the serum IL-10 levels in (A) were analyzed using an unpaired two-tailed t-test (*p<0.05, **p<0.01).

FIG. 6 shows results of identifying that the locally delivered hybrid spheroids reduce local immunoactivation and promote production of immune regulatory T cell (Treg): (A) is a schematic diagram showing the pancreatic islet cell isolation process on day 12 after transplantation for analysis; (B) is the result of identifying relative expression (n=3) of genes encoding perform (PRF1), granzyme B (GRMB), IFN-γ (IFNG), TNF-α (TNF), IL-10, TGF-β1, and FoxP3 (FOXP3); (C) is the result of a representative image for multiple immunohistochemical staining of a transplant; and (D) is flow cytometry evaluation (n=6) of T cell populations in RAP-MP and hybrid HS100 groups, wherein the data in (B) was analyzed using a one-way ANOVA test and (D) is the result of analysis using an unpaired two-tailed t-test (*p<0.05, **p<0.01, #p<0.001).

FIG. 7 shows results of identifying the role of MSC-mediated PD-L1 on the survival of pancreatic islet cell xenotransplants: (A) and (B) are the results of identifying the retention status of GFP-expressing MSCs in pancreatic islet cell xenotransplants over time, expressed by the remaining GFP signal intensity (n=3); (C) is the result of identifying the relative PD-L1 gene expression (n=3) in the whole transplant including pancreatic islet cells and naïve spheroids or hybrid HS100 evaluated on day 12 after transplantation; (D) to (F) are results of application in that mice transplanted with hybrid HS100 pancreatic islet cells were treated with anti-PD-L1 antibody therapy (2.5 mg/kg/dose×2 doses on days 10 and 20, intraperitoneal route; n=6); (D) is a schematic diagram illustrating the experimental process; (E) is the result of identifying NBG; (F) is a Kaplan-Meier curve graph for the survival time of pancreatic islet cell xenotransplants, wherein transplanted mice administered with each isotype control antibody were used as a control (n=3); (G) and (H) are the results of in-vitro and in-vivo identification for the surface protein expression of PD-L1 by MSCs in naïve spheroids and hybrid HS100 using flow cytometry, wherein, in (G), spheroids were cultured with or without a cytokine cocktail for 3 days before evaluation (n=2 in each group), and in (H), MSCs were labeled with carboxyfluorescein diacetate succinimidyl ester (CFDA-SE) prior to spheroid preparation for pancreatic islet cell transplantation, the transplants were collected on the day 7 for evaluation (n=3), and MSCs were considered as expressing PD-L1 in the case of double-positive CFDA-SE*PD-L1+; and (I) to (K) are the results of identifying the effect of PD-L1 expression by MSCs on the survival of pancreatic islet cell xenotransplants, wherein (I) is a schematic illustration of the experimental processes in that MSCs were transfected with PD-L1 siRNA or scrambled siRNA (50 nM, respectively) prior to transplantation, (J) is the result of checking non-fasting blood glucose (NBG), and (K) is the result of a Kaplan-Meier curve for the survival time (n=5) of xenotransplanted pancreatic islet cells.

DETAILED DESCRIPTION

Hereinafter, the present disclosure will be described in more detail.

The present disclosure relates to a technology for providing spheroids including mesenchymal stem cells and rapamycin microparticles, wherein the rapamycin microparticles increase PD-L1 expression of mesenchymal stem cells such that it was found that the spheroids with increased PD-L1 expression on the surface suppressed T cells and inflammatory responses that induce immune rejection to the transplanted pancreatic islet cells in vivo, thereby showing the effect of maintaining the survival period and insulin secretion function of the transplanted pancreatic islet cells for a long time. The inventors of the present disclosure have completed the present disclosure to provide the spheroid including the mesenchymal stem cells and rapamycin microparticles as a composition for suppressing immune rejection of a cell transplant.

The present disclosure may provide spheroids which include mesenchymal stem cells and rapamycin microparticles and in which PD-L1 expression is increased.

The rapamycin microparticles may include 0.1 to 50 parts by weight of rapamycin and 50 to 99.9 parts by weight of a polymer based on 100 parts by weight of the microparticles.

The polymer may be selected from the group consisting of poly(lactic-co-glycolic acid) (PLGA), chitosan, hyaluronic acid, collagen, gelatin, and albumin.

The mesenchymal stem cells may include $1\times10^4$ to $3\times10^4$ cells per spheroid.

The mesenchymal stem cells (MSCs) may be derived from adipose tissue, but is not limited thereto.

The rapamycin may be included in an amount of 10 to 200 ng per spheroid.

The spheroids may be one in which PD-L1 expression of mesenchymal stem cells is increased by rapamycin, and immune rejection of the transplant is suppressed by increased PD-L1 expression.

The transplant may be one or more endocrine cells selected from the group consisting of stem cells, pancreatic islet cells, epithelial cells, fibroblasts, osteoblasts, chondrocytes, cardiomyocytes, hepatocytes, human-derived cord blood cells, endothelial progenitor cells, and myoblasts.

The present disclosure may provide a composition for suppressing immune rejection, including the spheroids as an active ingredient.

The present disclosure may provide a method of preparing spheroids for suppressing immune rejection of a transplant, including preparing rapamycin microparticles in which rapamycin is encapsulated with a polymer (first operation); preparing a suspension by mixing the rapamycin microparticles and mesenchymal stem cells in a growth medium (second operation); preparing cell-particle fusion spheroids by injecting the suspension into a polymer solution and then culturing the same (third operation); and collecting the spheroids (fourth operation).

The suspension of the third operation may include $1\times10^4$ to $3\times10^4$ mesenchymal stem cells in 2 μl of a growth medium and 10 to 200 ng of rapamycin.

The third operation may be to condense the cell particles by injecting the suspension into the polymer solution and then culturing the same for 1 to 3 hours at 37° C.

The polymer solution may be a methyl cellulose solution.

In addition, the present disclosure may provide a cell therapy composition for preventing or treating diabetes, including the spheroids and pancreatic islet cells as active ingredients.

The transplant may include $0.1\times10^6$ to $5\times10^6$ mesenchymal stem cells and 200 to 5000 pancreatic islet equivalents (IEQs) of islet cells.

In the spheroid, PD-L1 expression is increased, and immune rejection for the transplanted pancreatic islet cells is suppressed to prolong the survival period and insulin release period of the pancreatic islet cells.

Hereinafter, to help the understanding of the present disclosure, example embodiments will be described in detail. However, the following example embodiments are merely illustrative of the content of the present disclosure, and the scope of the present disclosure is not limited to the following example embodiments. The example embodiments of the present disclosure are provided to more completely explain the present disclosure to those of ordinary skill in the art.

EXPERIMENTAL EXAMPLE

The following experimental examples are intended to provide experimental examples commonly applied to each example embodiment according to the present disclosure.

1. Preparation of RAP-MPs and Characteristic Analysis

Rapamycin (RAP) was encapsulated into PLGA microspheres (RAP-MP) using an oil-in-water emulsification (T. T. Nguyen, et al., Biomaterials 221, 119415, 2019). Briefly, poly(lactic-co-glycolic acid) (PLGA), Resomer RG504 H (76 mg; Sigma-Aldrich), and RAP (4 mg; LC Laboratories, Woburn, MA) were dissolved in dichloromethane (1 mL; Junsei Chemical, Japan). Next, the organic phase was homogenized in polyvinyl alcohol (PVA, 1%, 5 mL; Sigma-Aldrich) solution at 21,000 rpm for 4 minutes to prepare an emulsion. After stabilizing the emulsion in an excess of PVA solution for 4 hours, RAP-MP was collected from 5 cycles of centrifugal washing operation, and finally, RAP-MP was lyophilized to obtain dry powder for further experiments. The size of RAP-MP and chemical properties of RAP were checked using a scanning electron microscope (SEM, S-4100; Hitachi, Tokyo, Japan) and Fourier transform infrared spectroscopy (FT-IR; Nicolet *Nexus* 670 FTIR Spectrometer, Thermo Fisher Scientific), respectively.

In addition, the loading capacity of RAP-MP was determined by HPLC method. Briefly, RAP was extracted from RAP-MP using acetonitrile (ACN) and filtered through a 0.22 μm membrane.

Chromatographic parameters were as follows: Inertsil column (4.6×150 mm, 5 μm; GL Sciences, Tokyo, Japan), isocratic mobile phase in which ACN: $H_2O$ (85:15) is included per 1 ml/min, peak detection at 280 nm, and 60° C. for column temperature.

The in vitro release test for RAP-MP was performed in phosphate buffered saline (PBS, pH 7.4) in which 10% Tween 20 is contained. The microsphere suspension was incubated while keeping a shaking incubator (SI-64, 150; Hanyang Scientific Equipment Co., Ltd., South Korea) at 37° C. and 150 rpm.

At each determined time point, the supernatant was collected to quantify RAP levels.

2. Isolation of Mouse Adipocyte-Derived Mesenchymal Stem Cells (MSCs) and Characteristic Analysis All animal experiments were approved by the Institutional Review Board of Yeungnam University in Korea in accordance with national guidelines. Mesenchymal stem cells were isolated from C57BL6 mice (male, 8-10 week-old; Samtako, South Korea) by a method slightly modified from the previous protocol (P. Anderson, et al., Bio-protocol 5, e1642-e1642, 2015; G. Yu, et al., Methods Mol. Biol. 702, 29-36, 2011).

Briefly, mice were sacrificed by cervical dislocation, sterilized by immersing in 70% ethanol, and collected by exposing subcutaneous adipose tissue, cut into small pieces, and digested with 0.1% collagenase type P solution at 37° C. at 80 rpm for 30 minutes.

Thereafter, complete MEM-α medium was added to neutralize the enzyme activity, and then centrifuged at 400×g for 5 minutes to pelletize the cells. The cell pellets were re-dispersed in the complete MEM-α medium and residual fibers and large adipocytes were removed using a 40-μm cell strainer.

The cells collected after centrifugation were cultured at 37° C. overnight. The next day, the attached cells were carefully washed with PBS to remove residues and other suspending cells. The medium was frequently replaced every 2 to 3 days until MSCs meet 80-90% confluence. MSCs were used within 3-6 passages (p3-6) to ensure good results.

Characterization of the isolated MSCs was conducted on the specific cell surface markers (CD29, CD44, CD90, Sca-1, CD11b, CD34, and CD45) as well as differentiability into three lineages through assessment using previous protocols (M. C. Ciuffreda, et al., Mesenchymal Stem Cells, M. Gnecchi, Ed. (Springer New York, 2016), vol. 1416 of Methods in Molecular Biology, 149-158).

3. Preparation of Hybrid Spheroids

Hybrid spheroids were prepared using a free water-absorbing polymer-based method (N. Kojima, et al., Biomaterials 33, 4508-4514, 2012). In this study, 2% methylcellulose (Sigma-Aldrich) was added to the polymer solution for a complete MEM-α growth medium.

In the case of a single hybrid spheroid, 25,000 MSCs and RAP-MP were thoroughly mixed in the growth medium to prepare 2 μl of particle suspension, and then the suspension was slowly injected into a high-viscosity methylcellulose solution. Incubation was carried out at 37° C. for 2 hours to facilitate spontaneous cell particle condensation.

Hybrid spheroids were collected after lowering the viscosity of the methylcellulose solution by adding the growth medium. The collected hybrid spheroids were washed twice with the growth medium to completely remove methylcellulose prior to the culture in a non-adhesive Petri dish. RAP-MP hybrid spheroids, in which 10 ng, 40 ng, 100 ng, and 200 ng of RAP were contained respectively, were prepared and named HS10, HS40, HS100, and HS200, respectively.

MSC spheroids in which RAP-MP is not mixed were used as a control (naïve spheroid). To visualize RAP-MPs in hybrid spheroids, they were labeled with coumarin-6.

4. Shape and Size Distribution of Spheroids

Morphology of the naïve and hybrid spheroids was observed under a microscope system (Eclipse Ti; Nikon Instruments Inc., Melville, NY). Size distribution was measured by randomly selecting at least 30 spheroids using Nis-Element software.

5. Microsphere Distribution of Hybrid Spheroids

The distribution of microspheres in the hybrid spheroids was first observed under confocal laser scanning microscopy (CLSM; Nikon Alsi, Nikon Instruments Inc., Melville, NY).

Briefly, hybrid spheroids were collected on day 3 of culture, washed twice with PBS, and immobilized with 4% paraformaldehyde (PFA) solution (Sigma-Aldrich). Next, cell nuclei were counterstained with Hoechst 33342 solution (1:1000; Thermo Fisher Scientific) at room temperature for 20 minutes. Next, the sample was scanned, a 3D image of the spheroid was reconstructed in Nis-Element software, and Cou6-MPs and cell nuclei were labeled in green and blue, respectively.

In addition, hybrid spheroids were observed according to the previous protocol (C. Heckman, et al., Protocol Exchange (2007), doi:10.1038/nprot.2007.504.) using SEM (S-4100; Hitachi, Tokyo, Japan). Briefly, samples were immobilized with 4% glutaraldehyde solution for 60 minutes and then continuously stained with 1% OsO4, 3% carbohydrazide, and 1% OsO4 for 15 minutes respectively. All materials were purchased from Tokyo Chemical Industry (Tokyo, Japan). To expose the central structure in SEM, the hybrid spheroids were cut in half using a sharp blade before spray-coating with a platinum layer.

6. Identification of Cell Viability

Live/dead staining assay was performed to identify cell viability. Briefly, the naïve and hybrid spheroids were collected and incubated with a solution in which 0.67 μM acridine orange (AO) and 75 μM propidium iodine (PI) (both from Sigma-Aldrich) are contained at room temperature for 30 minutes, and then viable and dead cells were visualized with a fluorescence microscopy system (Eclipse Ti; Nikon Instruments Inc., Melville, NY) after performing green staining with AO and red staining with PI, respectively.

In addition, the apoptotic state of the cells was observed via Western blot using the previous protocol (T. T. Nguyen, et al., J Control Release 321, 509-518, 2020). Briefly, the naïve and hybrid spheroids were collected, separated into single cells by washing twice with PBS and mincing, and lysed with MPER lysis buffer (Thermo Fisher Scientific) on ice. Next, 30-40 μg of the total protein identified by the Pierce Protein Assay 660 nm kit (Thermo Fisher Scientific) was separated on a 12% SDS-PAGE gel and transferred to a PVDF membrane (Immobilon-P, Merck Millipore).

Next, blocking was performed with Tris buffer (containing 0.05% Tween 20) in which 5% BSA is contained at room temperature for 1 hour, and then incubation was followed using rabbit anti-Bax antibody (1:1000; Cell Signaling) or rabbit anti-GAPDH antibody (1:1000; Cell Signaling) overnight at 4° C. After washing, the membrane was incubated with anti-rabbit IgG-HRP (1:5000, Santa Cruz) at room temperature for 1 hour. Finally, the membrane was incubated with SuperSignal West Pico Chemiluminescent Substrate solution (Thermo Fisher Scientific) and detected using a Fujifilm LAS-4000 mini system (Fujifilm, Tokyo, Japan).

7. LC/MS/MS Analysis

RAP levels in hybrid spheroids were identified using LC/MS/MS.

Briefly, 1 to 3 hybrid spheroids were collected in microtubes at each determined time point and washed twice with PBS. RAP was extracted by probe sonication treatment in the presence of 0.1-1.0 ml of ACN. Samples were diluted appropriately for LC/MS/MS analysis and filtered through a 0.22-μm membrane.

FK506 was used as an internal control to compensate for the matrix effect of the sample. LC/MS/MS parameters were as follows: Agilent 1260 Infinity HPLC system (Agilent Technologies, Santa Clara, CA) equipped with HPLC Atlatis dC18 column (2.1×150 mm, 3 μm; Water Corporation, Milford, MA). Extraction by a solvent containing ACN and 2 mM ammonium acetate buffer in a gradient mode (0-2.5 min: 90% ACN, 2.5-10.5 min: 5% ACN, 10.5-16.0 min: 90% ACN); flow rate of 250 μl/min; 60° C. for column temperature. API-400 triple quadrupole (AB SCIEX, Framingham, MA) tandem mass system; ionization method: electrospray, positive ion mode; detection mode: multiple reaction monitoring (MRM); m/z 931.8 864.6 ion transition observation.

8. Cytokine Treatment

To observe the status of MSC spheroids when exposed to inflammatory conditions, a cytokine cocktail in which TNF-α (10 ng/ml; Novus Biologicals, LLC, CO) and IFN-α (20 ng/ml; Biolegend) are contained was treated. Naïve and hybrid spheroids were collected at predetermined time points, washed twice with PBS, and subjected to flow cytometry or real-time PCR.

9. Isolation of Rat Pancreatic Islets

Spague-Drague rats (male, 8-10 week-age; Samtako, South Korea) were used as pancreatic islet donors. Briefly, rats were sacrificed by cervical dislocation and the pancreas was exposed, followed by injection of a 0.08% collagenase type P solution (Sigma-Aldrich) through the hepatobiliary duct. The pancreas was degraded by incubation at 37° C. for 18 min. Pancreatic islets were isolated from exocrine cells by Histopaque-1077 solution (Sigma-Aldrich) gradient method. Finally, prior to transplantation, pancreatic islets were cultured in a complete RPMI medium for 3 days for functional recovery.

10. Cell Transplantation into C57BL/6 Mice

For cell transplantation, streptozocin-induced diabetic C57BL/6 mice (male, 8-10 week-age; Samtako, South Korea) were used as recipients. Non-fasting blood glucose (NBG) levels were periodically measured using the blood in the tail vein to check diabetic status satisfying NBG>350 mg/dL for 2 consecutive days.

Thereafter, the kidney was exposed to create a hole under the capsule. 400 IEQ islet cells with or without 20 spheroids ($0.5\times10^6$ MSCs) were prepared in a transplantation tube to be injected into the renal capsule cavity.

For RAP-MP delivery (without spheroids), particle suspension in approximately 5 μl of PBS (~5 μl) was loaded in transplantation tube and was separately injected to islet location. The transplants were considered to be rejected if NBG is greater than 200 mg/dL (NBG>200 mg/dL) for 2 consecutive days. In addition, intraperitoneal glucose tolerance test (IPGTT) was performed to check insulin secretion adaptation by transplanted islet cells to glucose tolerance (i.p, 2.0 g/kg).

11. Real-Time PCR

Quantitative real-time PCR analysis was performed to detect the changes in mRNA expression.

Spheroid samples were collected via in vitro analysis, washed twice with PBS, and then lysed with a TRIzol reagent (Thermo Fisher Scientific). Total mRNA was isolated from the supernatant aqueous phase by adding chloroform and further purified using a continuous precipitation method with isopropanol and ethanol for additional purification. For in vivo studies, mRNA was extracted from the transplant using the ReliaPrep™ RNA Tissue Miniprep kit (Promega, Madison, WI). Next, according to the manufacturer's instructions, cDNA was synthesized with the isolated mRNA using the GoScript™ Reverse Transcription Kit (Promega, Madison, WI).

Then, PCR amplification was performed using a suitable primer pair (Table 1) and SYBR Green kit (Thermo Fisher Scientific). The relative expression level of the target mRNA was calculated by the comparative threshold (Ct) method, which is to normalize the target mRNA Ct value to a GAPDH or 18S rRNA value.

TABLE 1

| Gene | Forward primer sequence | Reverse primer sequence |
|---|---|---|
| COX-1 | TCGGAGCCCCAGATATAGCA (SEQ ID NO: 1) | TTTCCGGCTAGAGGTGGGTA (SEQ ID NO: 2) |
| COX-2 | GGGCTCAGCCAGGCAGCAAAT (SEQ ID NO: 3) | GCACTGTGTTTGGGGTGGGCT (SEQ ID NO: 4) |
| IL1RN | TAGCAAATGAGCCACAGACG (SEQ ID NO: 5) | ACATGGCAAACAACACAGGA (SEQ ID NO: 6) |
| IL4 | TCAACCCCCAGCTAGTTGTC (SEQ ID NO: 7) | TGTTCTTCGTTGCTGTGAGG (SEQ ID NO: 8) |
| IL6 | ACAACCACGGCCTTCCCTACTT (SEQ ID NO: 9) | CACGATTTCCCAGAGAACATGTG (SEQ ID NO: 10) |
| IL10 | CCAGGGAGATCCTTTGATGA (SEQ ID NO: 11) | CATTCCCAGAGGAATTGCAT (SEQ ID NO: 12) |

TABLE 1-continued

| Gene | Forward primer sequence | Reverse primer sequence |
|---|---|---|
| TGFB1 | TTGCTTCAGCTCCACAGAGA (SEQ ID NO: 13) | TGGTTGTAGAGGGCAAGGAC (SEQ ID NO: 14) |
| IDO1 | GCTTTGCTCTACCACATCCAC (SEQ ID NO: 15) | CAGGCGCTGTAACCTGTGT (SEQ ID NO: 16) |
| INOS | GCTCGCTTTGCCACGGACGA (SEQ ID NO: 17) | AAGGCAGCGGGCACATGCAA (SEQ ID NO: 18) |
| HO-1 | GGTGATGGCTTCCTTGTACC (SEQ ID NO: 19) | AGTGAGGCCCATACCAGAAG (SEQ ID NO: 20) |
| MHC-I | GGCAATGAGCAGAGTTTCCGAG (SEQ ID NO: 21) | CCACTTCACAGCCAGAGATCAC (SEQ ID NO: 22) |
| MHC-II | GTGTGCAGACACAACTACGAGG (SEQ ID NO: 23) | CTGTCACTGAGCAGACCAGAGT (SEQ ID NO: 24) |
| CD86 | GATTATCGGAGCGCCTTTCT (SEQ ID NO: 25) | CCACACTGACTCTTCCATTCTT (SEQ ID NO: 26) |
| PD-L1 | TGCGGACTACAAGCGAATCACG (SEQ ID NO: 27) | CTCAGCTTCTGGATAACCCTCG (SEQ ID NO: 28) |
| PRF1 | TCATCATCCCAGCCGTAGT (SEQ ID NO: 29) | ATTCATGCCAGTGTGAGTGC (SEQ ID NO: 30) |
| GRMB | ACTCTTGACGCTGGGACCTA (SEQ ID NO: 31) | AGTGGGGCTTGACTTCATGT (SEQ ID NO: 32) |
| IFNG | TTCTTCAGCAACAGCAAGGC (SEQ ID NO: 33) | TCAGCAGCGACTCCTTTTCC (SEQ ID NO: 34) |
| TNF | TAGCCAGGAGGAGAACAGAAAC (SEQ ID NO: 35) | CCAGTGAGTGAAAGGGACAGAAC (SEQ ID NO: 36) |
| FOXP3 | CCTGGTTGTGAGAAGGTCTTCG (SEQ ID NO: 37) | TGCTCCAGAGACTGCACCACTT (SEQ ID NO: 38) |
| GAPDH | ACCACAGTCCATGCCATCAC (SEQ ID NO: 39) | TCCACCACCCTGTTGCTGTA (SEQ ID NO: 40) |
| 18S RNA | TCAACACAGGGATCGGACAACACA (SEQ ID NO: 41) | GCCTTGGATCAAGTTCACAGGCAA (SEQ ID NO: 42) |

12. Qualification of Mouse Serum Cytokine

Whole blood was collected from the heart of the recipient by cardiac puncture.

After the blood was left to clot at room temperature for 15 to 30 minutes, the serum was separated from the blood by centrifugation at 2000×g at 4° C. for 10 minutes, and the separated serum was stored at −80° C. until use. To quantify cytokine levels, the BD CBA Mouse Th1/Th2/Th17 Cytokine kit (Thermo Fisher Scientific) was used according to the manufacturer's instructions. Data were analyzed using Flowjo software version 7.6.2 (Becton, Dickinson & Company).

13. Flow Cytometry

Surface markers of MSCs and immune cells were identified by fluorescence-activated cell sorting (FACS) analysis. In general, MSC spheroids or lymphoid organs (spleen, lymph nodes) were isolated into single cells and washed twice with PBS staining buffer in which 0.3% BSA is contained. Samples were incubated with specific fluorescence-bound antibody on ice for 30 minutes. After washing twice with staining buffer, cells were immobilized with 4% PFA solution (Sigma-Aldrich) and analyzed using FACSCalibur (BD Biosciences).

Intracellular antigen staining was performed according to the instructions provided by BD BioSciences. Each isotype control antibody was used to compensate for non-specific binding of IgG to the cell surface, and the results were processed using Flowjo software version 7.6.2 (Becton, Dickinson & Company).

14. Histological Study

In order to observe histomorphology at day 12 post-transplantation, transplant-bearing kidneys were collected. Samples were collected from recipients with rejected transplants and organ functional transplants (125 days) from some experiments. Samples were immobilized in 4% PFA solution (Sigma-Aldrich) for 1 to 2 days and then immersed in 30% sucrose solution (Alfa Aesar, Ward Hill, MA) for 3 days.

Next, 10 μm sections were prepared with a deep freezing microtome system (HM450; Thermo Fisher Scientific) and placed on a gelatin-coated glass slide. The sample was subjected to epitope recovery with citric acid buffer (pH 6.0, with 0.05% Tween-20) in a water bath at 98° C. for 30 minutes, and the activity of endogenous peroxidase was inhibited with 3% hydroxyperoxide for 15 minutes. A circle was made therearound using a hydrophobic pen to limit the stained area. In addition, triple immunohistochemical staining was performed according to the instructions provided by Vector Laboratories to co-stain the islets and T-cells of the transplants.

For each antigen staining, the non-specific binding was first blocked in the sections with a PBS solution in which 2%

BSA, 10% normal serum (Vector Laboratories), and 0.3% Triton X-100 were contained and then with avidin solution and biotin solution (Vector Laboratories) at room temperature for 15 minutes, respectively. The sections were then incubated with anti-insulin (1:300; ProteinTech, Suite 300 Rosemont, IL), anti-CD3 (1:300; Novus Biologicals, LLC, CO 80112), anti-Foxp3 (1:200; Biolegend), or anti-PDL1 (1:300; Cell Signaling) primary antibodies overnight at 4° C. After washing with PBS, the sections were incubated with a biotin-conjugated secondary antibody at room temperature for 1 hour, and then incubated with HRP-labeled ABC kit working solution at room temperature for 30 minutes. Signals were detected by incubation with ImmPACT-DAB (brown) substrate solution, ImmPACT-VIP (purple) substrate solution, or ImmPACT-SG (gray blue) substrate solution at room temperature for 2 to 15 minutes. After washing with PBS and drying, the sections were fixed with VectorMount-Permanent Mounting Medium (Vector Laboratories) before imaging using a microscope system.

<Example 1> Preparation of Rapamycin-Microparticle (RAP-MP) and Identification of Characteristics RAP-MP was successfully prepared by oil-in-water emulsification. As a result of identifying the characteristics of RAP-MP, it was found in the scanning electron microscope (SEM) image as shown in FIGS. 1A and 1B that RAP-MP had a smooth surface and a size range of 1 to 8 μm (mean±SD=4.4±1.7 μm). It was also determined that RAP was physically encapsulated in PLGA microspheres since a new peak did not appear in the FTIR spectrum of RAP-MP compared to blank-MP as shown in FIG. 1C. In addition, the loading capacity (LC) and encapsulation efficiency (EE) of RAP-MP determined by HPLC were 4.10±0.26% and 82.0±5.2%, respectively, and as shown in FIG. 1D, the release pattern of RAP-MP showed sustained release for RAP for 30 days with minimal burst during the first 2 days.

<Example 2> Identification of Characteristics of Mouse Adipose Tissue-Derived Mesenchymal Stem Cells (MSCs)

MSCs were isolated from subcutaneous adipose tissues of C57BL/6 mice according to standard protocols. The isolated MSCs exhibited a typical fibroblast morphology and were positive by 95% or higher (>95%) for a set of markers including CD29, CD44, CD90, and Sca-1, while being negative (<2%) for CD11b, CD34, and CD45. In addition, it was found that these MSCs have the ability to differentiate into the osteogenic lineage by deposition of calcium crystals stained with Alizarin red S, the adipogenic lineage by accumulation of Oil red O-stained lipid droplets, and the cartilage lineage by accumulation of glycosaminoglycans stained with Alcian blue.

<Example 3> Formation of Spheroids that are Uniform in Methylcellulose Solution Referring to FIG. 2A illustrating the preparation of spheroids using a methylcellulose solution, in principle, free water molecules are rapidly absorbed by the viscous methylcellulose solution after injection of a suspension of MSCs with or without microspheres (MP), resulting in promotion of spontaneous, stable formation of cell-particle hybrid spheroids within 2 hours due to a close contact between MSCs and MPs. In the present disclosure, a single hybrid spheroid was composed of $2.5\times10^4$ MSCs and various amounts of MP corresponding to 10, 40, 100, and 200 ng of RAP (HS10, HS40, HS100, and HS200 groups, respectively), and MP-free spheroids were defined as naïve spheroids. No significant change was found in the size of the different spheroids as shown in FIGS. 2B and 2C. For example, naïve spheroids and hybrid spheroids HS100 showed sizes of 740±47 μm and 744±32 μm on day 0, respectively (p=0.6849, t-test). Interestingly, as shown in FIGS. 2B to 2C, these spheroids showed a significant size reduction up to approximately 1.5-fold (~1.5-fold) 3 days after the culture as a result of cell-cell contraction over time (naïve spheroids: 492±32 μm and hybrid spheroids HS100: 478±21 μm).

Next, in an attempt to identify the MP distribution of hybrid spheroids on day 3 of the culture, confocal laser scanning microscopy (CLSM) and SEM image analysis for each of the hybrid HS100 were performed. As a result, as shown in CLSM in FIG. 2D, MPs labeled with Cou6-MP were entangled with blue-labeled cell nuclei and were uniformly distributed throughout the hybrid spheroid. In addition, in the SEM image, it was possible to observe the hybrid spheroid that the MP has morphology clearly distinguishable from the cell matrix. In addition, the density of MP in the hybrid spheroid was found to be proportional to the concentration of the added MP.

In addition, liquid chromatography tandem mass spectrometry (LC-MS/MS) analysis was used to determine the actual content of RAP in the hybrid spheroids. Referring to FIG. 2F, a total of 9.46±1.08 (capture efficiency, EE=94.6±10.8%), 38.34±4.54 (EE=95.8±11.4%), 98.08±10.98 (EE=98.1±11.0%), and 216.79±17.21 ng (EE=108.4±8.6%) of RAP were identified in each of the hybrid spheroids HS10, HS40, HS100, and HS200.

Next, the release pattern of RAP in hybrid spheroids was observed. Interestingly, similar RAP release profiles were observed in all groups regardless of the initial loading amount of RAP-MP. Referring to FIG. 2F, in particular, it was found that RAP was released by 50 to 70% in the first week and 10 to 20% in the second week, and then almost became extinct from the hybrid spheroid after 3 weeks. As shown in the above results, it was found that the RAP released from the hybrid spheroids appeared faster than in the RAP-MP suspension (FIG. 1D).

Preparation of large spheroids often causes problems concerning the cell viability due to limitations in nutrient and oxygen infiltration. However, as shown in FIG. 2G, it was found that the spheroids prepared in methylcellulose medium maintained high cell viability in the Live/Dead staining analysis on day 3, in contrast to the counterpart prepared by the hanging drop technique. In addition, as found in the western blot analysis, it was shown that the formation of spheroids significantly reduced the level of pro-apoptotic Bax protein compared to monolayer (two-dimensional, 2D) cultured cells. Moreover, incorporation of RAP-MP into hybrid spheroids further decreased Bax levels in a dose-dependent manner, but no significant changes appeared in the dead cell count (FIGS. 2G to 2I).

<Example 4> Identification of Enhancement of Immunomodulatory Gene Expression by MSC after Hybrid Spheroid Formation 3D cultured MSCs are known to exhibit enhanced immunomodulatory effects compared to 2D cultured MSCs. First, reverse transcription polymerase chain reaction (qRT-PCR) analysis was applied to observe dynamic changes in immunomodulatory gene expression of naïve spheroids in accordance with the culture time. To this end, naïve spheroids were prepared and cultured in MEM-α medium for 1-3 days. As a result, it was found that the expression of CD86, MHC-I, MHC-II, TGFB1, IL1RN, and IL4 significantly increased in accordance with the culture time as shown in FIG. 3B.

On day 1 of culture, a transient increase was observed in expression of INOS and HO-1 genes, but expression of PD-L1, IL6, and COX2 genes by naïve spheroids was significantly decreased after 3 days of culture. A cytokine cocktail containing 10 ng/ml TNF-α and 20 ng/ml IFN-γ was treated to the spheroids during the culture to mimic the inflammatory environment. Interestingly, as shown in FIG. 3B, it was found, compared to the untreated group, that the group exposed to the cytokine cocktail for 3 days showed significantly increased level of IDO (69.5±19.4-fold), iNOS (5.4±0.5-fold), PD-L1 (6.9±2.9-fold), MHC-1 (8.5±2.2-fold), and MHC-2 (1.8±0.5-fold).

Next, the effect of RAP-MP incorporation in hybrid spheroids was identified. Naïve spheroids and hybrid HS100 were cultured in the MEM-α growth medium with or without the cytokine cocktail as shown in FIG. 3. It was found, in the absence of the cytokine cocktail, that expression of COX-2 (2.3±0.5-fold, p=0.0102), IL6 (3.6±0.4-fold, p=0.0005), TGFB1 (3.1±0.8-fold, p=0.0096), and PD-L1 (1.4±0.1-fold, p=0.0001) was significantly increased on day 3 of culture, in hybrid HS100 rather than naïve spheroids. Notably, cytokine exposure further increased gene expression of MHC-I, IL10, and PD-L1 by 1.5±0.3-fold (p=0.0318), 1.7±0.1-fold (p<0.0001), and 2.0±0.1-fold, respectively, in hybrid HS100 (p<0.0001). However, on day 3, the gene expression levels of IDO1 and INOS decreased by 1.9±0.5 and 1.3±0.1-fold, respectively, as a result of RAP-MP incorporation.

<Example 5> Identification of Improvement in Survival of Xenogeneic Pancreatic Islet Cells by Localized Hybrid Spheroids in a Mouse Model To identify the prevention of strong immune response by hybrid spheroids, a pancreatic rat-to-mouse islet xenotransplant model was established. As shown in FIG. 4A, pancreatic islet cells (400 islet equivalents, IEQs) were transplanted alone (control) or with RAP-MPs, naïve spheroids or hybrid spheroids under the renal capsule of streptozocin (STZ)-induced diabetic C57BL/6 mice. 20 spheroids corresponding to $0.5\times10^6$ MSCs were used per transplant.

In addition, the total dose of RAP treated per transplant in the RAP-MP, hybrid HS10, HS40, HS100 and HS200 groups was determined to be 1534.0±499.8, 139.4±24.2, 538.3 24.6, 1378.2±87.0, and 2882.2±41.0 ng (p=0.6225 in RAP-MP vs. HS100).

Non-fasting blood glucose (NBG) levels and Kaplan-Meier transplant survival curves of pancreatic islet cell recipients were identified as shown in FIGS. 4B and 4C, respectively. As identified, the mean survival time (MST) for the transplant of pancreatic islet cells of the control was 9 days (mean±standard deviation (SD)=9.2±0.8 days), resulting in early rejection. Co-transplantation of naïve spheroids and pancreatic islet cells did not show any improvement in pancreatic islet cell viability with 7 days of MST (mean±SD=7.2±1.8 days; p=0.0518 vs control). On the other hand, local single dose RAP-MP delivery prolonged pancreatic islet cell survival by approximately 2-fold compared to the control. In particular, the MST of the RAP-MP group was 18.5 days (mean±SD=21.2±7.5 days, p=0.0008 vs control). However, no function was detected in the pancreatic islet cell transplants of the RAP-MP group after 40 days.

From the above results, it was found that RAP-MP alone exhibited only temporary immunosuppression. However, local hybrid spheroids showed an effective protection for the pancreatic islet cell xenotransplants from strong immune rejection, and the effect was RAP dose-dependent. As shown in FIGS. 4B and 4C, recipients transplanted with HS10, HS40, HS100, and HS200 had survival period of MST 52 days (mean±SD=59.6±38.5 days), 62 days (mean SD=55.2±35.8 days), 61 days (mean±SD=69.9±22.9 days), and 95.5 days (mean±SD=75.4±34.9 days) (all p values<0.0001 vs control or vs naïve spheroid group).

In addition, of pancreatic islet cell recipients transplanted with hybrid spheroids, 79% (19 of 24), 17% (4 of 24), and 8% (2 of 24) maintained functions for more than 50 days, 100 days, and 125 days, respectively. Organ transplant acceptance (>125 days) was identified in two recipients of hybrid HS10 (n=1) and HS100 (n=1) (black circles; FIG. 4B). RAP levels in the serum of the hybrid HS100 group were barely detectable at the time of analysis (<1 ng/ml).

On the other hand, to evaluate the sustained release requirement of RAP for immune protection, naïve spheroids pretreated with 100 nM RAP solution for 3 days and pancreatic islet cells were co-transplanted.

As a result, the naïve spheroid group showed early pancreatic islet cell transplant rejection (MST=10 days), similar as the control group. In addition, since individual transplantation of pancreatic islet cells and hybrid HS100 in the contralateral renal capsule caused the initial rejection (MST=10 days, p=0.1842 vs control), it was found that local delivery of hybrid spheroids to the pancreatic islet cell region was essential to exhibit immune protection. (Also identified was whether hybrid spheroids formed of human MSCs may exhibit a protective effect for pancreatic islet cell xenotransplant survival. Consequently, co-transplantation of human MSCs-derived hybrid HS100 with pancreatic islet cells did not prevent initial rejection (MST=9 days, p=0.7319 vs control).)

At day 12 post-transplantation, an intraperitoneal glucose tolerance test (IPGTT) was performed to evaluate the reactivity of pancreatic islet cell transplant upon glucose overload.

As a result, as shown in FIGS. 4D and 4E, the localized hybrid HS100 group and the RAP-MP group responded normally to glucose elevation as in the non-diabetic (normal) mice. In contrast, as it was found that the hypoglycemic effect of the control and naïve spheroid groups was delayed, the pancreatic islet cells of the control and naïve spheroid groups were not viable.

<Example 6> Identification of Immunomodulatory Effect of Local Hybrid Spheroids To investigate immune responses, blood, spleen (SPL), draining lymph nodes (DLN), and transplants were collected on day 12 post-transplantation. Serum isolated from whole blood was used to measure cytokine levels with a cytometric bead array (CBA) mouse Th1/Th2/Th17 cytokine kit.

As a result, as shown in FIG. 5A, significantly increased in transplantation of control pancreatic islet cells (islet only) were serum levels of inflammatory and anti-inflammatory cytokines including IL-2 (26.0±18.8 pg/ml, p=0.006), IL-4 (28.6±19.1 pg/ml, p=0.0037), IL-6 (27.1±17.9 pg/ml, p=0.0038), IL-10 (32.6±15.8 pg/ml, p=0.0022), IL-17 (36.5±32.3 pg/ml), IFN-γ (31.0±21.8 pg/ml, p=0.013), and TNF-α (30.6±17.9 pg/ml, 0.0144) (All p values vs normal mice, one-way ANOVA test; unpaired two tailed t-test was applied for IL-10). Interestingly, the locally delivered hybrid spheroid group showed significantly reduced levels of IL-2 (5.4±1.1 pg/ml, p=0.0074), IL-4 (6.9±3.0 pg/ml, p=0.0046), IL-6 (5.5±2.1 pg/ml, p=0.0048), IFN-γ (7.7±2.6 pg/ml, p=0.0153), and TNF-α (11.1±3.2 pg/ml, p=0.0345) (all p values vs control). On the other hand, such cytokine levels appeared to be slightly reduced in the naïve spheroid and RAP-MP groups compared to the control. In addition, no significant change was found in the serum level of IL-10 in the pancreatic islet cell transplant group.

To evaluate the progression of immunoactivation, the IFN-γ/IL-10 ratio that reflects the balance in the Th1/Th2 population in the blood was calculated. As a result, as shown in FIG. 5B, a decrease was shown in the ratio of IFN-γ/IL-10 as the following order: the control (0.90±0.29), naïve spheroids (0.84±0.11), RAP-MP (0.61±0.26), and hybrid HS100 (0.54±0.23, p=0.0411 vs control; unpaired two-tailed t-test). From the above results, it was found that the local delivery of the hybrid spheroids showed low immunoactivation.

Next, to perform flow cytometry, immune cells from DLN and SPL were harvested, and the percentage of each immune cell population was calculated based on the total cell counts. As a result of performing flow cytometry, it was determined that there was no significant change in the total $CD4^+$ and $CD8^+$ T cell percentage between the transplanted groups in the two lymphoid organs as shown in FIG. 5C.

Nevertheless, the ratio of CD4+:$CD8^+$ T cell population in DLN showed a tendency to decrease in the control and naïve spheroid groups. Notably, compared to the control, the local delivery of hybrid HS100 drastically decreased production of effector memory $CD8^+CD44^{high}CD62^{low}$ W T cell ($CD8^+$ TEM) (DLNs: 3.44±0.73% versus 5.01±1.24%, p=0.2127; SPL: 0.23±0.06% vs 0.35±0.08%, p=0.0144) and central memory $CD8^+CD44^{high}CD62^{high}$ T cell ($CD8^+$ $T_{CM}$) (DLNs: 1.29±0.30% vs 2.35±0.43%, p=0.0235; SPL: 1.32±0.31% vs 1.77±0.22%, p=0.1786). Moreover, it was found that hybrid HS100 promoted the production of $CD4^+$ $FoxP3^+$ T cells ($CD4^+$ $T_{reg}$) in DLN (2.67±0.81% vs 1.68±0.26% of the naïve spheroid group, p=0.0355).

Next, the transplant-bearing kidney was collected to observe the local immune response. Immune-related gene expression in the transplant was analyzed by qRT-PCR.

As a result, as shown in FIG. 6A, the hybrid HS100 group showed a significant decrease in the expression of PRF1 (perform) and IFNG (IFN-γ), whereas the expression of TGFB1 (TGF-β1) and FOXP3 (FoxP3) was significantly increased (minimum 3-fold difference compared to control, p<0.05). In addition, the expression of granzyme B (GRMB) and IL10 showed a tendency to decrease and increase, respectively, as a result of hybrid HS100 delivery. Surprisingly, no significant change in TNF (TNF-α) was observed among the transplanted groups. Moreover, it was found that the gene expression profile of the RAP-MP group was similar to that of the hybrid HS100 group at this time point (12 days after transplantation), except for low expression of TGFB1 and FOXP3.

In addition, histomorphological characteristics of the pancreatic islet cell xenotransplants were identified by performing hematoxylin & eosin (H&E) and multi-immunohistochemical staining.

As a result, a number of host cells infiltrating T cells (blue staining) were observed in the control group and the naïve spheroid group as shown in FIG. 6C, while dissociated insulin-positive pancreatic islet cells (brown staining) were decreased. In contrast, co-localization of pancreatic islet cells with hybrid HS100 or RAP-MP reduced general host cell recruitment to the transplant at an early stage after transplantation. However, most of the pancreatic islet cells were intact in the hybrid HS100 transplants, whereas they were destructed in the RAP-MP transplants due to rejection by T cell invasion. Interestingly, we were able to identify the most abundant FoxP3-positive regulatory T cells (Treg; purple staining) among the infiltrating T cells in the hybrid HS100 group.

In addition, in order to quantitatively detect immune cell populations, pancreatic islet cell transplants of hybrid HS100 and RAP-MP groups were collected on day 12, separated into single cells, and subjected to flow cytometry.

As a result, as shown in FIG. 6D, there was no relative difference in the number of $CD8^+$ T cells, but an increase in the $CD4^+$ T cell counts as well as the ratio of $CD4^+$:$CD8^+$ T cells in the hybrid HS100 group. In addition, the delivery of hybrid HS100 significantly increased the absolute number and percentage of $CD4^+$ $T_{reg}$ cells in the transplant compared to sole delivery of RAP-MP.

From the above results, it was found that locally delivered hybrid spheroids diminished systemic immunoactivation and promoted formation of $T_{reg}$ cell populations to prevent initial rejection of pancreatic islet cell transplants.

<Example 7> Identification of Immunomodulation Through Enhanced PD-L1 Expression in Hybrid Spheroids First, after transplantation of naïve spheroids or hybrid HS100 along with pancreatic islet cells, the survival of MSCs was tracked. To this end, green fluorescent protein (GFP)-expressing MSCs were used to fabricate spheroids. Then, the transplant-bearing kidney was collected and imaged by detecting the GFP signal. As a result, as shown in FIGS. 7A and 7B, the GFP intensity in both groups decreased dramatically over time. However, the GFP expression and retention time of MSCs in the hybrid HS100 group were significantly enhanced compared to the naïve spheroid group. In particular, GFP signal was remained by 25.5±16.10% vs 0.7±1.0%, on day 10 (p=0.019). On day 20, GFP signal in hybrid HS100 group was still detected (6.4±3.5%), but not in the naïve spheroid group.

Since PD-L1 plays an important role in immunomodulation, the gene expression of PD-L1 was identified in whole pancreatic islet cell xenotransplants 12 days after transplantation. Referring to FIG. 7C, interestingly, the hybrid HS100 group had much higher gene levels of PD-L1 than the naïve spheroid group (3.1±1.7-fold vs 1.1±0.7-fold).

In addition, the role of PD-L1 on survival time of pancreatic islet cell xenotransplants was identified. Pancreatic islet cells were transplanted along with hybrid HS100 under the renal capsule of diabetes-induced mice. Then, on day 10 and 20, mice were intraperitoneally injected with double doses of anti-PD-L1 antibody solution or each isotype control antibody solution (2.5 mg/kg/dose each). As a result of observing NBG as shown in FIG. 7D, the pancreatic islet cell transplant was rejected immediately after treatment of anti-PD-L1 antibody, and MST was determined to be 18 days (p<0.01 vs isotype control) as shown in FIGS. 7E and 7F.

From the above results, a hypothesis was formulated that PD-L1 expressed by MSCs transplanted from hybrid spheroids may be involved in the immunomodulatory effect in vivo. Therefore, the surface expression of PD-L1 by MSCs was observed by flow cytometry. Spheroids were cultured with or without treatment of a cytokine cocktail containing 20 ng/ml IFN-γ and 10 ng/ml TNF-α for 3 days prior to evaluation.

As a result, as shown in FIG. 7G, it was found that PD-L1 was expressed on the surface of MSC even in a non-stimulated state (without the cytokine cocktail), and expression increased dramatically after exposure to the cytokine cocktail. Surprisingly, hybrid HS100 consistently exhibited higher levels of PD-L1 in both unstimulated and stimulated conditions with changes by 1.31±0.04-fold and 3.14±0.29-fold, respectively, compared to naïve spheroids (p value<0.01).

In addition, the expression of PD-L1 by the transplanted spheroids in vivo was measured. To this end, MSCs were labeled with carboxyfluorescein diacetate succinimidyl ester (CFDA-SE) prior to fabrication of spheroids for pancreatic islet cell transplantation, and the transplants were collected on day 7 for flow cytometry. As a result, as shown in FIG. 7H, it was found that the percentage of the $CFDA-SE^+$ $PD-L1^+$ MSC population was higher in the transplant including the hybrid HS100 than in the naïve spheroids (94.1±2.6% vs. 89.2±3.8%, respectively). Importantly, a significantly high level of surface PD-L1 abundance was detected, as the higher median fluorescence intensity (p=0.038) observed in hybrid HS100. To investigate the role of PD-L1 expressed by MSCs for the survival of pancreatic islet cell xenotransplants, MSCs were repeatedly transfected with 50 nM PD-L1 siRNA or 50 nM scrambled siRNA prior to transplantation as shown in FIG. 7I.

As a result, as shown in FIGS. 7J and 7K, pancreatic islet cell transplants including hybrid HS100 transfected with PD-L1 siRNA were initially discontinued while showing MST of 22 days, whereas the group transfected with scrambled siRNA remained functional even at day 40 (p=0.0256 vs scrambled siRNA group).

From the above results, it was found that enhanced PD-L1 expression by MSCs in hybrid HS100 improved MSC maintenance and survival rate of pancreatic islet cell xenotransplants.

As described above, a specific part of the content of the present disclosure was described in detail, for those of ordinary skill in the art, it is clear that this specific description is only a preferred embodiment, and the scope of the present disclosure is not limited thereby. Accordingly, the substantial scope of the present disclosure may be defined by the appended claims and equivalents thereof.

What is claimed is:

1. Spheroids for suppressing immune rejection of a transplant, each of the spheroids comprising:

$1\times10^4$ to $3\times10^4$ mesenchymal stem cells; and rapamycin microparticles in which rapamycin is microencapsulated with poly(lactic-co-glycolic acid), the rapamycin microparticles being physically incorporated and distributed among the mesenchymal stem cells within each of the spheroids, wherein each of the spheroids comprises 10 to 200 ng of rapamycin, wherein the rapamycin microparticles provide sustained release of rapamycin within each of the spheroids, and wherein PD-L1 expression of the mesenchymal stem cells is increased by the rapamycin released from the rapamycin microparticles, leading to suppression of immune rejection of the transplant.

2. The spheroids of claim 1, wherein the rapamycin microparticles comprise, with respect to 100 parts by weight of the microparticles, 0.1 to 50 parts by weight of the rapamycin and 50 to 99.9 parts by weight of the poly(lactic-co-glycolic acid).

3. The spheroids of claim 1, wherein the rapamycin microparticles have a mean diameter of 1 to 8 μm.

4. The spheroids of claim 1, wherein the transplant is one or more cells selected from the group consisting of stem cells, pancreatic islet cells, epithelial cells, fibroblasts, osteoblasts, chondrocytes, cardiomyocytes, hepatocytes, human-derived cord blood cells, endothelial progenitor cells, and myoblasts.

5. A composition for suppressing immune rejection, comprising the spheroids of claim 1 as an active ingredient.

6. A method of preparing the spheroids of claim 1 for suppressing immune rejection of a transplant, the method comprising:

preparing rapamycin microparticles in which rapamycin is encapsulated with poly(lactic-co-glycolic acid) (first operation);

preparing a suspension by mixing the rapamycin microparticles and mesenchymal stem cells in a growth medium (second operation);

preparing cell-particle fusion spheroids by injecting the suspension into a polymer solution and then culturing the same (third operation); and collecting the spheroids (fourth operation).

7. The method of claim 6, wherein the suspension of the third operation comprises $1\times10^4$ to $3\times10^4$ mesenchymal stem cells in 2 μl of a growth medium and 10 to 200 ng of rapamycin.

8. The method of claim 6, wherein the third operation is to condense cell particles by injecting the suspension into a methyl cellulose solution and then culturing the same at 37° C. for 1 to 3 hours.

9. A method of treating type I diabetes, comprising:

administering a cell therapy composition comprising the spheroids of claim 1 and pancreatic islet cells as active ingredients to a subject in need thereof.

10. The method of claim 9, comprising 200 to 5000 islet equivalents (IEQs) of the pancreatic islet cells.

11. The method of claim 9, wherein the spheroids in which PD-L1 expression is increased and immune rejection for transplanted pancreatic islet cells is suppressed prolong a survival period and an insulin release period of pancreatic islet cells.

* * * * *

SEQUENCE LISTING

```
Sequence total quantity: 42
SEQ ID NO: 1            moltype = DNA  length = 20
FEATURE                 Location/Qualifiers
source                  1..20
                        mol_type = other DNA
                        organism = synthetic construct
SEQUENCE: 1
tcggagcccc agatatagca                                              20

SEQ ID NO: 2            moltype = DNA  length = 20
FEATURE                 Location/Qualifiers
source                  1..20
                        mol_type = other DNA
                        organism = synthetic construct
SEQUENCE: 2
tttccggcta gaggtgggta                                              20

SEQ ID NO: 3            moltype = DNA  length = 21
FEATURE                 Location/Qualifiers
source                  1..21
                        mol_type = other DNA
                        organism = synthetic construct
SEQUENCE: 3
gggctcagcc aggcagcaaa t                                            21

SEQ ID NO: 4            moltype = DNA  length = 21
FEATURE                 Location/Qualifiers
source                  1..21
                        mol_type = other DNA
                        organism = synthetic construct
SEQUENCE: 4
gcactgtgtt tggggtgggc t                                            21

SEQ ID NO: 5            moltype = DNA  length = 20
FEATURE                 Location/Qualifiers
source                  1..20
                        mol_type = other DNA
                        organism = synthetic construct
SEQUENCE: 5
tagcaaatga gccacagacg                                              20

SEQ ID NO: 6            moltype = DNA  length = 20
FEATURE                 Location/Qualifiers
source                  1..20
                        mol_type = other DNA
                        organism = synthetic construct
SEQUENCE: 6
acatggcaaa caacacagga                                              20
```

```
SEQ ID NO: 7            moltype = DNA  length = 20
FEATURE                 Location/Qualifiers
source                  1..20
                        mol_type = other DNA
                        organism = synthetic construct
SEQUENCE: 7
tcaaccccca gctagttgtc                                              20

SEQ ID NO: 8            moltype = DNA  length = 20
FEATURE                 Location/Qualifiers
source                  1..20
                        mol_type = other DNA
                        organism = synthetic construct
SEQUENCE: 8
tgttcttcgt tgctgtgagg                                              20

SEQ ID NO: 9            moltype = DNA  length = 22
FEATURE                 Location/Qualifiers
source                  1..22
                        mol_type = other DNA
                        organism = synthetic construct
SEQUENCE: 9
acaaccacgg ccttccctac tt                                           22

SEQ ID NO: 10           moltype = DNA  length = 23
FEATURE                 Location/Qualifiers
source                  1..23
                        mol_type = other DNA
                        organism = synthetic construct
SEQUENCE: 10
cacgatttcc cagagaacat gtg                                          23

SEQ ID NO: 11           moltype = DNA  length = 20
FEATURE                 Location/Qualifiers
source                  1..20
                        mol_type = other DNA
                        organism = synthetic construct
SEQUENCE: 11
ccagggagat cctttgatga                                              20

SEQ ID NO: 12           moltype = DNA  length = 20
FEATURE                 Location/Qualifiers
source                  1..20
                        mol_type = other DNA
                        organism = synthetic construct
SEQUENCE: 12
cattcccaga ggaattgcat                                              20

SEQ ID NO: 13           moltype = DNA  length = 20
FEATURE                 Location/Qualifiers
source                  1..20
                        mol_type = other DNA
                        organism = synthetic construct
SEQUENCE: 13
ttgcttcagc tccacagaga                                              20

SEQ ID NO: 14           moltype = DNA  length = 20
FEATURE                 Location/Qualifiers
source                  1..20
                        mol_type = other DNA
                        organism = synthetic construct
SEQUENCE: 14
tggttgtaga gggcaaggac                                              20

SEQ ID NO: 15           moltype = DNA  length = 21
FEATURE                 Location/Qualifiers
source                  1..21
                        mol_type = other DNA
                        organism = synthetic construct
SEQUENCE: 15
gctttgctct accacatcca c                                            21

SEQ ID NO: 16           moltype = DNA  length = 19
FEATURE                 Location/Qualifiers
source                  1..19
                        mol_type = other DNA
                        organism = synthetic construct
SEQUENCE: 16
```

```
caggcgctgt aacctgtgt                                                    19

SEQ ID NO: 17          moltype = DNA  length = 20
FEATURE                Location/Qualifiers
source                 1..20
                       mol_type = other DNA
                       organism = synthetic construct
SEQUENCE: 17
gctcgctttg ccacggacga                                                   20

SEQ ID NO: 18          moltype = DNA  length = 20
FEATURE                Location/Qualifiers
source                 1..20
                       mol_type = other DNA
                       organism = synthetic construct
SEQUENCE: 18
aaggcagcgg gcacatgcaa                                                   20

SEQ ID NO: 19          moltype = DNA  length = 20
FEATURE                Location/Qualifiers
source                 1..20
                       mol_type = other DNA
                       organism = synthetic construct
SEQUENCE: 19
ggtgatggct tccttgtacc                                                   20

SEQ ID NO: 20          moltype = DNA  length = 20
FEATURE                Location/Qualifiers
source                 1..20
                       mol_type = other DNA
                       organism = synthetic construct
SEQUENCE: 20
agtgaggccc ataccagaag                                                   20

SEQ ID NO: 21          moltype = DNA  length = 22
FEATURE                Location/Qualifiers
source                 1..22
                       mol_type = other DNA
                       organism = synthetic construct
SEQUENCE: 21
ggcaatgagc agagtttccg ag                                                22

SEQ ID NO: 22          moltype = DNA  length = 22
FEATURE                Location/Qualifiers
source                 1..22
                       mol_type = other DNA
                       organism = synthetic construct
SEQUENCE: 22
ccacttcaca gccagagatc ac                                                22

SEQ ID NO: 23          moltype = DNA  length = 22
FEATURE                Location/Qualifiers
source                 1..22
                       mol_type = other DNA
                       organism = synthetic construct
SEQUENCE: 23
gtgtgcagac acaactacga gg                                                22

SEQ ID NO: 24          moltype = DNA  length = 22
FEATURE                Location/Qualifiers
source                 1..22
                       mol_type = other DNA
                       organism = synthetic construct
SEQUENCE: 24
ctgtcactga gcagaccaga gt                                                22

SEQ ID NO: 25          moltype = DNA  length = 20
FEATURE                Location/Qualifiers
source                 1..20
                       mol_type = other DNA
                       organism = synthetic construct
SEQUENCE: 25
gattatcgga gcgcctttct                                                   20

SEQ ID NO: 26          moltype = DNA  length = 22
FEATURE                Location/Qualifiers
source                 1..22
                       mol_type = other DNA
                       organism = synthetic construct
```

```
SEQUENCE: 26
ccacactgac tcttccattc tt                                              22

SEQ ID NO: 27           moltype = DNA  length = 22
FEATURE                 Location/Qualifiers
source                  1..22
                        mol_type = other DNA
                        organism = synthetic construct
SEQUENCE: 27
tgcggactac aagcgaatca cg                                              22

SEQ ID NO: 28           moltype = DNA  length = 22
FEATURE                 Location/Qualifiers
source                  1..22
                        mol_type = other DNA
                        organism = synthetic construct
SEQUENCE: 28
ctcagcttct ggataaccct cg                                              22

SEQ ID NO: 29           moltype = DNA  length = 19
FEATURE                 Location/Qualifiers
source                  1..19
                        mol_type = other DNA
                        organism = synthetic construct
SEQUENCE: 29
tcatcatccc agccgtagt                                                  19

SEQ ID NO: 30           moltype = DNA  length = 20
FEATURE                 Location/Qualifiers
source                  1..20
                        mol_type = other DNA
                        organism = synthetic construct
SEQUENCE: 30
attcatgcca gtgtgagtgc                                                 20

SEQ ID NO: 31           moltype = DNA  length = 20
FEATURE                 Location/Qualifiers
source                  1..20
                        mol_type = other DNA
                        organism = synthetic construct
SEQUENCE: 31
actcttgacg ctgggaccta                                                 20

SEQ ID NO: 32           moltype = DNA  length = 20
FEATURE                 Location/Qualifiers
source                  1..20
                        mol_type = other DNA
                        organism = synthetic construct
SEQUENCE: 32
agtggggctt gacttcatgt                                                 20

SEQ ID NO: 33           moltype = DNA  length = 20
FEATURE                 Location/Qualifiers
source                  1..20
                        mol_type = other DNA
                        organism = synthetic construct
SEQUENCE: 33
ttcttcagca acagcaaggc                                                 20

SEQ ID NO: 34           moltype = DNA  length = 20
FEATURE                 Location/Qualifiers
source                  1..20
                        mol_type = other DNA
                        organism = synthetic construct
SEQUENCE: 34
tcagcagcga ctccttttcc                                                 20

SEQ ID NO: 35           moltype = DNA  length = 22
FEATURE                 Location/Qualifiers
source                  1..22
                        mol_type = other DNA
                        organism = synthetic construct
SEQUENCE: 35
tagccaggag gagaacagaa ac                                              22

SEQ ID NO: 36           moltype = DNA  length = 23
FEATURE                 Location/Qualifiers
source                  1..23
                        mol_type = other DNA
```

-continued

```
                        organism = synthetic construct
SEQUENCE: 36
ccagtgagtg aaagggacag aac                                   23

SEQ ID NO: 37           moltype = DNA  length = 22
FEATURE                 Location/Qualifiers
source                  1..22
                        mol_type = other DNA
                        organism = synthetic construct
SEQUENCE: 37
cctggttgtg agaaggtctt cg                                    22

SEQ ID NO: 38           moltype = DNA  length = 22
FEATURE                 Location/Qualifiers
source                  1..22
                        mol_type = other DNA
                        organism = synthetic construct
SEQUENCE: 38
tgctccagag actgcaccac tt                                    22

SEQ ID NO: 39           moltype = DNA  length = 20
FEATURE                 Location/Qualifiers
source                  1..20
                        mol_type = other DNA
                        organism = synthetic construct
SEQUENCE: 39
accacagtcc atgccatcac                                       20

SEQ ID NO: 40           moltype = DNA  length = 20
FEATURE                 Location/Qualifiers
source                  1..20
                        mol_type = other DNA
                        organism = synthetic construct
SEQUENCE: 40
tccaccaccc tgttgctgta                                       20

SEQ ID NO: 41           moltype = DNA  length = 24
FEATURE                 Location/Qualifiers
source                  1..24
                        mol_type = other DNA
                        organism = synthetic construct
SEQUENCE: 41
tcaacacagg gatcggacaa caca                                  24

SEQ ID NO: 42           moltype = DNA  length = 24
FEATURE                 Location/Qualifiers
source                  1..24
                        mol_type = other DNA
                        organism = synthetic construct
SEQUENCE: 42
gccttggatc aagttcacag gcaa                                  24
```